United States Patent [19]
Mohr

[11] Patent Number: 5,405,343
[45] Date of Patent: Apr. 11, 1995

[54] BLOOD BAG SYSTEM

[75] Inventor: Harald Mohr, Hannover, Germany

[73] Assignee: Blutspendedienst der Landesverbande des Deutschen Roten Kreuzes Niedersachsen, Oldenburg und Bremen G GmbH, Germany

[21] Appl. No.: 108,741
[22] PCT Filed: Jan. 20, 1992
[86] PCT No.: PCT/DE92/00031
§ 371 Date: Sep. 2, 1993
§ 102(e) Date: Sep. 2, 1993
[87] PCT Pub. No.: WO92/15274
PCT Pub. Date: Sep. 17, 1992

[30] Foreign Application Priority Data
Mar. 7, 1991 [DE] Germany ............... 9102709 U

[51] Int. Cl.$^6$ ............... A61B 19/00; A61M 5/32
[52] U.S. Cl. ............... 604/416; 604/56; 604/82; 604/83; 604/84; 604/85; 604/87; 604/92; 604/403; 128/DIG. 24
[58] Field of Search ............... 604/56, 82–92, 604/403–404, 408–410, 416, 905; 128/760, 771, DIG. 13, DIG. 24, 912; 422/44

[56] References Cited
U.S. PATENT DOCUMENTS
3,874,384  4/1975  Deindoerfer et al. ............... 604/408
5,304,113  4/1994  Sieber et al. ............... 604/4

Primary Examiner—Randall L. Green
Assistant Examiner—P. Zuttarelli
Attorney, Agent, or Firm—Bierman and Muserlian

[57] ABSTRACT

The invention is directed to a blood bag system for blood products comprising a bag (3) and at least one tubing (11) connected thereto, the system being made of at least partly transparent plastics material, wherein photoactive substances (31) may be enclosed in a closed-off section (A) of the tubing (11) of the ready-for-use system, which may be handled individually as an independent unit. Every blood bag system of this kind is adapted to be combined with another blood bag system, which may comprise one or several bags (3, 5, 7, 9) and may likewise be handled as an independent unit, by interconnecting both systems.

9 Claims, 1 Drawing Sheet

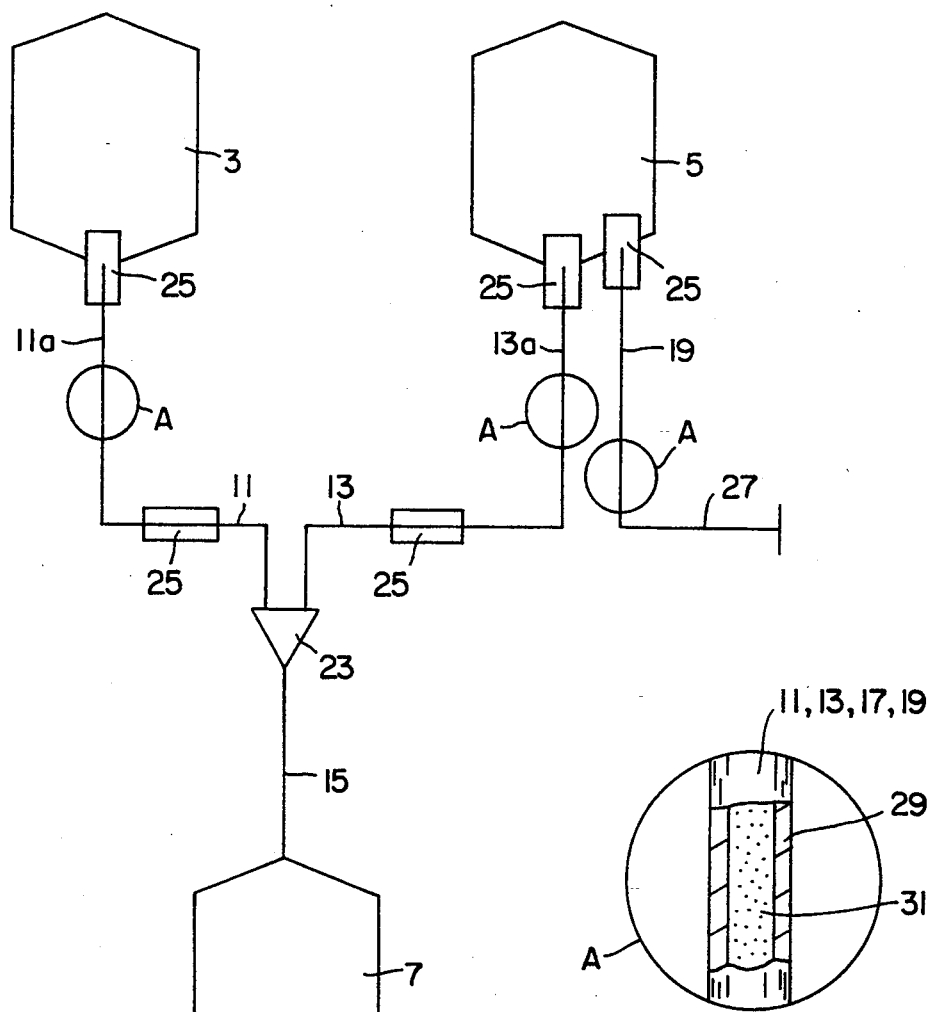
FIG. 1
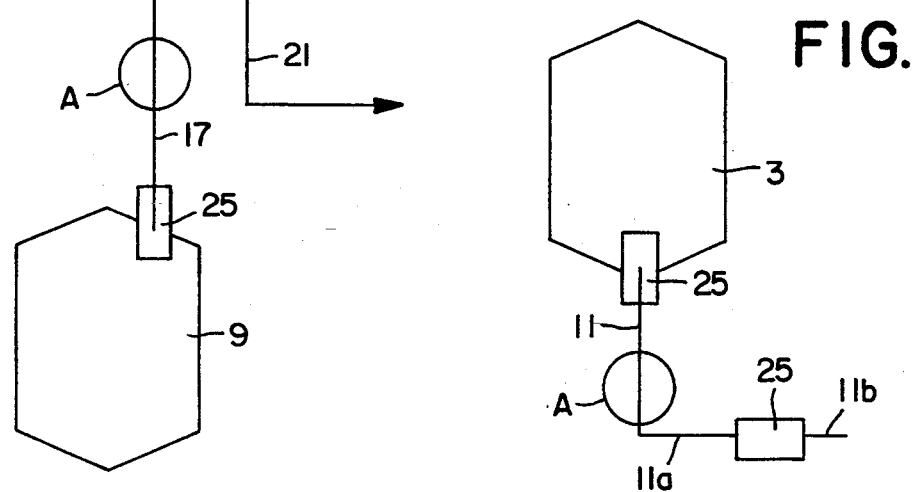
FIG. 1a
FIG. 2

BLOOD BAG SYSTEM

The invention is directed to a blood bag system for donor blood and/or blood products comprising a bag and at least one tubing connected thereto, the system being composed of at least partly transparent plastics material.

Prior blood bag systems by means of which donor blood is collected and processed comprise a collection bag and/or one or several further bags connected thereto and interconnected by tubings. The bags are made of a flexible plastic sheet material; the tubings are likewise made of flexible plastics. The plastics materials of bags and tubings are at least partly transparent. The bags are used, on the one hand, for collecting blood or blood fractions into which the donor blood is separated by centrifuging, for instance plasma, thrombocytes and erythrocytes, and on the other hand for accommodating special washing or additive solutions.

Working with blood bags poses the particular problem that the preparation introduced into the sterile blood bag may contain viruses which need to be inactivated.

It is the objective of the invention to provide a blood bag system in which the blood or blood components from individual donors may be rendered virus-safe or may be stored in virus-safe fashion, wherein the means for rendering the blood or the blood components virus-safe are stored up to the time of use in sections of the system which are necessary for blood processing.

With a blood bag system for donor blood and/or blood products comprising a bag and at least one tubing connected thereto, the system being made of at least partly transparent plastics material, the above-specified objective is achieved in accordance with the invention in that photoactive substances (31) can be enclosed in a closed-off section of the tubing of the ready-to-use system, which can be handled individually as an independent unit.

Likewise, with a blood bag system for donor blood and/or blood products comprising bags and tubings made of at least partly transparent plastics material, in which the tubings interconnect the bags and/or are connected to other tubings, the above-specified objective is achieved in accordance with the invention in that photoactive substances can be enclosed in closed-off sections of the tubings of the ready-to-use system, which can be handled individually as an independent unit.

When photoactive substances are placed in the tubings of the blood bag systems during manufacture thereof, and when these substances are co-sterilized in the blood bag system, it is possible upon use to perform in said blood bag systems by means of said additives a treatment, especially virus inactivation of the donor blood or blood plasma, by exposing the blood bag systems to light after the donor blood has been combined with said photoactive substances. The photoactive substances exhibit the property of being stimulated by light and of emitting energy, which results in the inactivation of viruses possibly present in the preparation.

Furthermore, with a blood bag system for donor blood and/or blood products comprising at least one bag and at least one tubing connected thereto by means of which the bags may be connected otherwise, wherein the system is at least partly made of transparent plastics material, the specified objective is achieved by the feature that a blood bag system which is independent and may be handled individually and comprises a bag and a tubing which encloses photoactive substances in closed-off sections thereof, may be combined with another blood bag system which is likewise independent and to be handled individually and consists of a bag and a tubing or several bags with tubings interconnecting said bags, by interconnecting said blood bag systems.

Thus, one of the two blood bag systems may be free from photoactive substances. While virus inactivation is fully effective, it is possible to provide one of the combined systems at less expense.

The combination may be effected by coupling a tubing of one blood bag system to a tubing of the other blood bag system with the aid of a welding device under sterile conditions.

In accordance with a further development of the second embodiment of the invention the bags are constituted by a collection bag and further bags connected thereto. In this way processing of the donor blood may be performed in an initially closed system.

In accordance with a further development of the second embodiment the invention provides that in case of a multi-bag system, collection bag and further bags are interconnected via tubings which enclose substances. Thus, processing of the donor blood may be performed from the outset within a self-contained system.

The substances may be enclosed in the tubings by means of frangible valves. Due to enclosure within the tubings it is ensured that the substances are ready everywhere to come into contact with the blood or blood fractions. The opening of the tubing connections by breaking the frangible valves allows the enclosed substances to be brought into contact with the blood or blood fractions in controlled fashion.

According to a preferred embodiment of the invention the photoactive substances are provided in liquid or dissolved state, respectively. The liquid state of aggregation permits particularly fast combining of the photoactive substances with the blood or blood fractions.

A further development of the invention provides that the photoactive substances used are phenothiazine dyes, preferentially methylene blue or toluidine blue.

The invention will be explained in detail with reference to the drawing, in which:

FIG. 1 shows a multi-bag blood bag system for donor blood in which the individual bags are interconnected through frangible valves and tubings and photoactive substances are enclosed in tubing sections, FIG. 1a shows an enlarged detail A of a tubing section filled with a photoactive substance, FIG. 2 shows a single blood bag system comprising a single bag and a tubing with photoactive substances enclosed within the tubing. This blood bag system can be handled individually as an independent unit and may be welded to a multi-bag blood bag system of FIG. 1, which can likewise be handled individually as an independent unit.

FIG. 1 shows a multi-bag blood bag system comprising two satellite bags 3, 5, a collection bag 7 and a bag 9 for an additive solution. The satellite bag 3 and the collection bag 7 as well as the satellite bag 5 and the collection bag 7 are interconnected via tubings 11, 13. A tubing end 19 closed at the free end 27 thereof and called a pigtail is provided on the satellite bag 5. A collection tubing 21 is fitted to the collection bag 7. The tubings 11 and 13 leading from the satellite bags 3 and 5 are joined by a one-way valve 23. In this way they are communicated via a common tubing 15 with the collection bag 7.

Within the tubing 11 there is a central section 11a which in the ready-to-use state of the blood bag system is closed by frangible valves 25. Likewise, the tubing 13 includes a central section 13a which in the ready-to-use state is closed on either side by means of frangible valves 25. The tubing end 19 which is closed at the free end 27 thereof is coupled to the satellite bag 5 by means of another frangible valve 25.

The frangible valves, which are only schematically illustrated, are of known design. They are injection-moulded plastic articles including a through-channel the passage through which is initially blocked upon manufacture by means of a co-injected membrane or the like. The frangible valves are so-called disposable valves and are configured so that the blockage of the through-passage is cancelled upon bending. The membrane is removed upon bending. The passage is then open and an exchange of media may take place via the through-channel.

A tubing 17 provides direct communication between the collection bag 7 and the additive bag 9. The connections between the tubing 17 and the bags 7 and 9 are provided by frangible valves 25. A collection tubing 21 is coupled to the collection bag via a further frangible valve 25.

In FIG. 1, sections of the tubings 11, 13, 19 and 17 are emphasized by circles referenced A. These sections A are shown extremely enlarged in FIG. 1a. This is a sectional view of the tubing sections. The cut-out area shows that the tubing sections 11a, 13a, 17, 19 contain a photoactive substance 31 between the tubing walls 29. In the ready-to-use state the photoactive substances 31 are enclosed between the frangible valves 25 within the tubing sections 11a, 13a, 17, 19. By breaking of the valves 25 the photoactive substances are allowed to flow into the respective bags 3, 5, 7, 9.

FIG. 2 shows a single-bag blood bag system comprising a bag 3 provided with a tubing 11. The tubing 11 opens into the bag 3 via a frangible valve 25. Also, a further frangible valve 25 is provided in the tubing 11 at a distance from the frangible valve 25 on the bag 3, whereby a closed-off tubing section 11a is formed. A photoactive substance 31 is enclosed within the closed-off tubing section 11a. This is indicated by the detail A which corresponds to the configuration of FIG. 1a. Initially, the free end 11b of the delivery tubing 11 is not connected.

The free end 11b of the delivery tubing 11 may, for example, be coupled with a tubing of the blood bag system of FIG. 1.

For this, a welding device may be used for welding, and thus connecting the free end 11b for instance to the tubing 15 of FIG. 1.

For the purposes of the invention, the photoactive substances are used as liquids 31. Of course, it would also be possible to use them in solid state (for instance as powders).

When it is desired that the blood plasma or a cellular blood fraction should be combined with the photoactive substance the frangible valves 25 are opened by breaking. In this way the bag system remains self-contained so that there is no risk at all of a bacterial infection. Analogously, it would of course be possible also to equip other systems comprising a greater or lesser number of bags with photoactive substances in the same way.

Examples of useful photoactive substances are phenothiazine dyes. Among those, the most suitable ones are methylene blue and toluidine blue.

We claim:

1. A ready-to-use blood bag system for donor blood or blood products comprising a bag (3) and at least one tube (11) connected thereto, the system being made of at least partially transparent plastic material and photoactive substances (31) enclosed in a closed-off section of the tube of the ready-to-use system with a frangible valve in the tube between the bag (3) and the closed off section.

2. A ready-to-use blood bag system for donor blood or blood products comprising a bag (3) and at least one tube (11) connected thereto, the system being made of at least partly transparent plastics material, wherein photoactive substances (31) are enclosed in a closed-off section (A) of the tube (11) of the ready-to-use system and a frangible valve (25) is in the tube between the bag and the photoactive substances (11), which can be handled individually as an independent unit.

3. The blood bag system as claimed in claim 2, wherein the tubings (11) of the one blood bag system are adapted to be welded to tubes (11, 13, 15, 17, 21) of the other blood bag system.

4. The blood bag system as claimed in claim 2, wherein in the photoactive substances (31) are provided in the liquid or dissolved state, respectively.

5. The blood bag system as claimed in claim 2, wherein phenothiazine dyes are provided as said photoactive substances (31).

6. The blood bag system as claimed in claim 5, wherein methylene blue or toluidine blue are provided as said dyes.

7. A ready-to-use blood bag system for donor blood or blood products comprising bags (3, 5, 7, 9) and tubes (11, 13, 15, 17) made of at least partly transparent plastics material, said tubes (11, 13, 15, 17) interconnecting the bags (3, 5, 7, 9) or being connected to other tubes (19, 21) wherein photoactive substances (31) are enclosed in closed-off sections (A) of the tubes (11, 13, 15) of the ready-to-use system and a frangible valve (25) is in the tubes having photoactive substances therein, the valve being between the photoactive substances and the other bags or tubes (11), which can be handled individually as an independent unit.

8. The blood bag system as claimed in claim 7, wherein in the case of the multi-bag system, collection bags (7) and further bags (3, 5, 9) are interconnected via tubes (11, 13, 15, 17) which have substances (31) enclosed therein.

9. A ready-to-use blood bag system for donor blood or blood products comprising at least one bag and at least one tube connected thereto through which the bags may be connected further, said material, wherein a blood bag system which is to be handled independently and individually and is composed of a bag (3) and tube (11) having photoactive substances (31) enclosed in closed-off sections (A), combined with another blood bag system which is to be handled independently and individually and which is composed of a bag (3) and a tube (11) or a plurality of bags (3, 5, 7, 9) and tubes (11, 13, 15, 17) interconnecting said bags and a frangible valve (25) is in the tubes having photoactive substances therein, the valve being between the photoactive substances and the other bags or tubes (11), by interconnecting said blood bag systems.

* * * * *